United States Patent
Hencken et al.

[11] Patent Number: 5,953,120
[45] Date of Patent: *Sep. 14, 1999

[54] OPTICAL PROBE

[75] Inventors: Kenneth Hencken, Pleasanton; William L. Flower, Livermore, both of Calif.

[73] Assignee: Sandia Corporation, Livermore, Calif.

[*] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/582,787

[22] Filed: Jan. 4, 1996

[51] Int. Cl.$^6$ ..................................................... G01N 21/00
[52] U.S. Cl. ............................................ 356/339; 356/338
[58] Field of Search ..................................... 356/336–340; 250/201.1, 201.2

[56] References Cited

U.S. PATENT DOCUMENTS

| | | | |
|---|---|---|---|
| 4,637,716 | 1/1987 | Auweter et al. | 356/28.5 |
| 4,871,251 | 10/1989 | Preikschat et al. | 356/336 |
| 5,112,127 | 5/1992 | Carrabba et al. | 356/301 |
| 5,231,463 | 7/1993 | Shambaugh | 356/336 |
| 5,313,542 | 5/1994 | Castonguay | 356/337 |
| 5,777,734 | 7/1998 | Flower et al. | 356/341 |

OTHER PUBLICATIONS

U.S. application No. 08/228,974, French et al., filed Apr. 15, 1994.
Dyott, "The Fibre–optic Doppler Anemometer", Microwaves, Optics, & Acoustics, vol. 2 (#1), p. 13 (Jan. 1978).

*Primary Examiner*—Robert H. Kim
*Assistant Examiner*—Amanda Merlino
*Attorney, Agent, or Firm*—Timothy Evans; Kurt Olsen

[57] ABSTRACT

A compact optical probe is disclosed particularly useful for analysis of emissions in industrial environments. The instant invention provides a geometry for optically-based measurements that allows all optical components (source, detector, rely optics, etc.) to be located in proximity to one another. The geometry of the probe disclosed herein provides a means for making optical measurements in environments where it is difficult and/or expensive to gain access to the vicinity of a flow stream to be measured. Significantly, the lens geometry of the optical probe allows the analysis location within a flow stream being monitored to be moved while maintaining optical alignment of all components even when the optical probe is focused on a plurality of different analysis points within the flow stream.

10 Claims, 1 Drawing Sheet

OPTICAL PROBE

STATEMENT OF GOVERNMENT INTEREST

This invention was made with Government support under contract no. DE-AC04-94AL8500 awarded by the U.S. Department of Energy to Sandia Corporation. The Government has certain rights in the invention.

BACKGROUND OF THE INVENTION

The present invention relates to a device for transmitting light to and receiving light from a remote sample for analysis and more particularly to an optical probe for use in measuring the optical response of a remote sample.

The ability to monitor particulate matter in process streams and emissions to the air from industrial operations, and particularly the ability to do so in-situ and in real-time, is becoming increasingly important in many industrial processes. This is the case not only because of the desire to control and modify various processes in real-time to improve their efficiency but also to comply with various environmental regulations governing the composition, quantity and quality of industrial emissions.

Air emissions of toxic, hazardous and regulated materials are coming under increasing scrutiny by the regulatory community. Not only are industrial operations being required to monitor their air emissions more closely but also they are being required to do so on a continuous basis. Measurement of hazardous metal concentrations in stack emissions is a difficult task. Currently, air emissions of these metals from industrial operations are measured using extractive sampling followed by off-line chemical analysis, a procedure that is costly and typically has long turnaround times. Furthermore, because of the many manual operations involved in extractive sampling there is a significant potential for introducing sampling errors. Complete analyses of stack measurements typically are not available for two to four weeks from the time that samples are collected. Furthermore, certification tests require that more than one sample be taken for a given operating condition and that at least one sample be taken for each operating condition. The long turnaround times inherent in extractive sampling prevent the use of air emissions measurements as a method of controlling operating parameters in real-time. Continuous measurements of industrial air emissions could ultimately provide real-time information that could be used by facility operators to modify operating parameters to improve efficiency or reduce air emissions. Although most of the metal air emissions are in the particulate phase, vapors may also be significant and must be measured simultaneously. Furthermore, the particles that contain metals may be quite inhomogeneous and particulate metals may be present in any of a large number of compounds.

Optical methods, because they can provide instantaneous data readouts, can generally be located within or in proximity to a flow stream (process stream or source of air emissions) and can be placed in remote locations, are particularly useful as a means of monitoring particulate air emissions and controlling operating parameters. Optical methods can be classified into two principle classes: one, wherein an output optical signal, produced in response to an input optical signal, is measured; two, wherein a change in the input optical signal, produced in response to the medium through which the input optical signal has traveled, is measured (i.e., a transmittance measurement).

A wide variety of instruments are currently available for on-line analysis of flow streams. However, the optical probes that these instruments use are typically designed for analysis of the concentration of constituents in fluid streams. These optical probes generally contain bundles of optical fibers and specialized lenses and mirrors that are not suitable for use in the harsh environments encountered in monitoring particulate emissions from industrial boilers, incinerators and furnaces. Furthermore, many of these instruments employ beam dividers or splitters, an arrangement which causes more than 75% of the available light to be lost. Because of the requirement for a second probe that receives light transmitted through the sample, instruments that operate in the transmittance mode are generally unsuited for use in the harsh environments of stack emissions from boilers, incinerators, furnaces and the like.

A method for circumventing many of the problems discussed above was disclosed in U.S. Pat. No. 4,637,716. Here, an anemometer measures light scattered from particles in a fluid, wherein an entrant light beam from a laser passes through a hole in a mirror inclined 45° to the beam axis and is focused by a focusing lens onto the end of an optical fiber. Scattered light collected by the optical fiber emerges from the fiber at a larger angle than the entrant light and is converted to a relatively large diameter beam by the focusing lens. The parallel beam of returning light is subsequently reflected by the inclined mirror into a detection system via a second lens system. While the method of getting light into and out of an analysis area described in the '716 patent overcomes many of the deficiencies noted earlier, this method does not permit focusing the entrant light beam on any particular area or particle selected for analysis within a flow stream. Furthermore, while optical fibers are useful for transmitting an incident light beam from a low power (~1–2 Watt) laser they are completely unsatisfactory for transmitting the high intensity incident light beam from a high power (~kilowatts) laser such as would be used for laser spark spectroscopy, for example, because of severe degradation of the optical fiber by the high intensity laser light.

For the reasons set forth above, it is highly desirable to have an optical probe that permits measurements to be made at a plurality of locations within a flow stream, is rugged enough to be used for monitoring emissions from industrial boilers, incinerators and furnaces and can introduce the optical input to the measurement location and extract the optical response through limited access ports in a chamber or duct enclosing the emissions. It is further desired that the probe should be reliable, suitable for remote sampling and easy to align and operate.

The instant invention provides an optical probe whereby all of its optical components (source, detector, relay optics, etc.) can be located in proximity to one another and generally exterior to the flow stream being monitored thereby permitting a compact and rugged system. The geometry of the optical probe disclosed herein provides a means for making optical measurements in environments where it is difficult and/or expensive to gain access to the vicinity of a measurement point from more than one direction, making it particularly useful for remote sampling operations in industrial environments. Most important, this optical probe geometry allows the measurement location to be moved within the flow stream being monitored while maintaining optical alignment of all optical components thus simplifying alignment and operation of the optical probe.

SUMMARY OF THE INVENTION

The optical probe of the present invention comprises a lens system for focusing an incident light beam onto a plurality of analysis locations within a flow stream being monitored and for collecting a return light beam from each of the plurality of analysis locations. The optical probe also includes means for separating the incident light beam from the return light beam whereby the return light beam can be transformed to provide a real-time analysis of material present at each of the analysis locations.

In one embodiment, the optical response to the incident light beam at an analysis location can be collected by a first lens that focused the incident light. The optical response, collimated by the first lens, is coaxial with the incident light beam but propagating in a direction opposite to that of the incident light. In a second embodiment an incident light beam is input to a focusing lens by means of inclined mirror. This embodiment is particularly advantageous, because it permits the light source to be mounted at an angle relative to the beam axis, e.g., perpendicular, rather than in-line thereby permitting a more compact monitoring instrument. By coaxially separating the collimated input light beam from the collimated response, the optical arrangement disclosed herein not only permits the incident light beam and the optical response beam to enter and exit the analysis point through the same aperture but also provides for moving the analysis location within the flow stream being monitored, while maintaining optical alignment of all components, simply by translating the first lens so that a new analysis point, located at the focal point of the first lens can be acquired; no further changes or adjustments are required. Measurements can be made at any of a plurality of locations in a flow stream comprising a gas, liquid, or aerosol or combinations thereof, or on a solid/gas, solid/liquid or liquid/gas interface, or internal to a transparent or partially transparent solid.

DETAILED DESCRIPTION OF THE INVENTION

The present invention relates generally to optical probes and particularly to a novel compact optical probe useful for measuring the optical response at an analysis point or within a small volume of a flow stream being monitored and is most particularly useful for monitoring particulate air emissions in various industrial operations and in the field.

To better understand the present invention, the following discussion is provided. If diverging light rays originate at the focal point of a lens system, they can be collimated by that lens system. Furthermore, if parallel light rays are incident on a lens system, the rays exiting from the lens system will converge to the focal point of the lens system. Thus, a system composed of two lenses that are positioned coaxially such that light that originates at the focal point of the first lens will be collimated by that first lens and will be incident on the second lens which, in turn, focuses that light onto the focal point of the second lens. Thus a plurality of analysis points can be acquired by simply translating the first lens and its associated focal point so that the new analysis point is located at the focal point of the first lens; and as a consequence, no further changes or adjustments are required in the second lens that still focuses the collimated return light, originating at the focal point of the first lens system, onto, for example, a transmitting/detecting means. On the other hand, if the return light from the first lens were diverging, any changes made in the position of the first lens would require compensating translational changes in the second lens that focuses the return light onto the transmitting/detecting means. Furthermore, the optical response from any point other than the focal point of the first lens will not be collimated by this lens and therefore will not be focused onto the transmitting/detecting means located at the focal point of the second lens and thus will not be efficiently measured.

Figure 1:
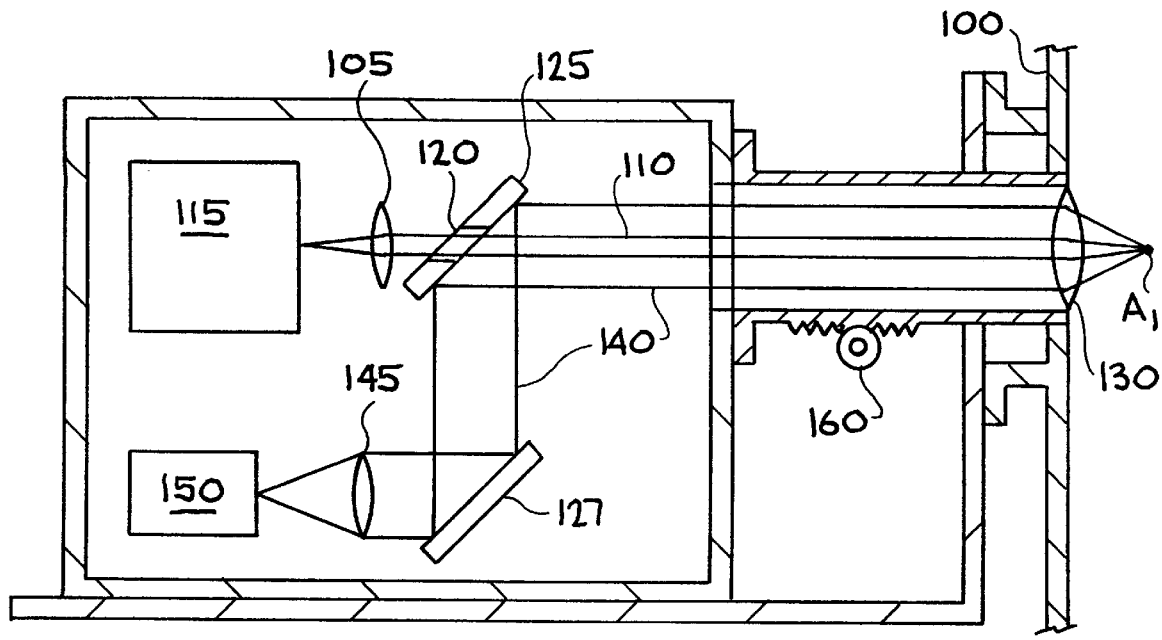
FIG. 1 shows a first embodiment of the instant invention.

A first embodiment of the optical probe of the instant invention is shown in FIG. 1. In the embodiment illustrated in FIG. 1, an optical probe can be used, for example, to analyze particles (not shown) present in the flow stream of an industrial stack (i.e. emissions) 100 by means of laser spark spectroscopy. Here, a light beam 110, issues from a light source 115, preferably a laser, and is collimated by collimating lens 105. The collimated beam 110 then passes through an aperture 120 in a mirror 125, the mirror being inclined at an angle to input beam 110. The collimated beam 110 can then be focused by focusing lens 130, onto a selected point $A_1$ within the stack, for analysis of the particles within a volume about analysis point $A_1$ (the analysis location). The optical response of the particles within the volume being analyzed is in the form of a return light beam 140 from analysis point $A_1$. The return light beam 140 is collected and collimated by focusing lens 130 and is reflected by mirror 125 and mirror 127 onto lens 145, which act in cooperation to provide means for focusing return light beam 140 onto light transmitting sensor 150, which can be the face of a optical fiber cable or bundle that transmits light to a detection means (not shown). For the purpose of simplifying further discussion, this coaxial, counterflow lens system will be hereafter referred to as a single-ended lens system to distinguish it from double-ended lens systems that require separate lens configurations; one for introducing the light beam into the flow stream (incident beam) and another for collecting the return light beam (optical response). The detection means can be preceded by a spectrometer or other wavelength selecting device. New analysis points $A_i$ (where i=1, 2, ..., n) within the stack can be acquired by translating lens 130 such that the focal point of lens 130 is focused on a different analysis point $A_i$ (not shown). No other changes in the optical probe are required.

A simple variation on this geometry can further reduce the number of optical components in the optical system. By curving the surface of mirror 125 (curved surface not shown), mirror 125 can also act as a focusing element. By positioning transmitting means 150 at the focal point of curved mirror 125 the collimated output beam 140 of light that originates at analysis point $A_i$ can be focused directly on the transmitting sensor 150 thereby eliminating the need for intermediate means to focus the return light beam (i.e., mirror 127 and lens 145) onto transmitting means 150.

Figure 2:
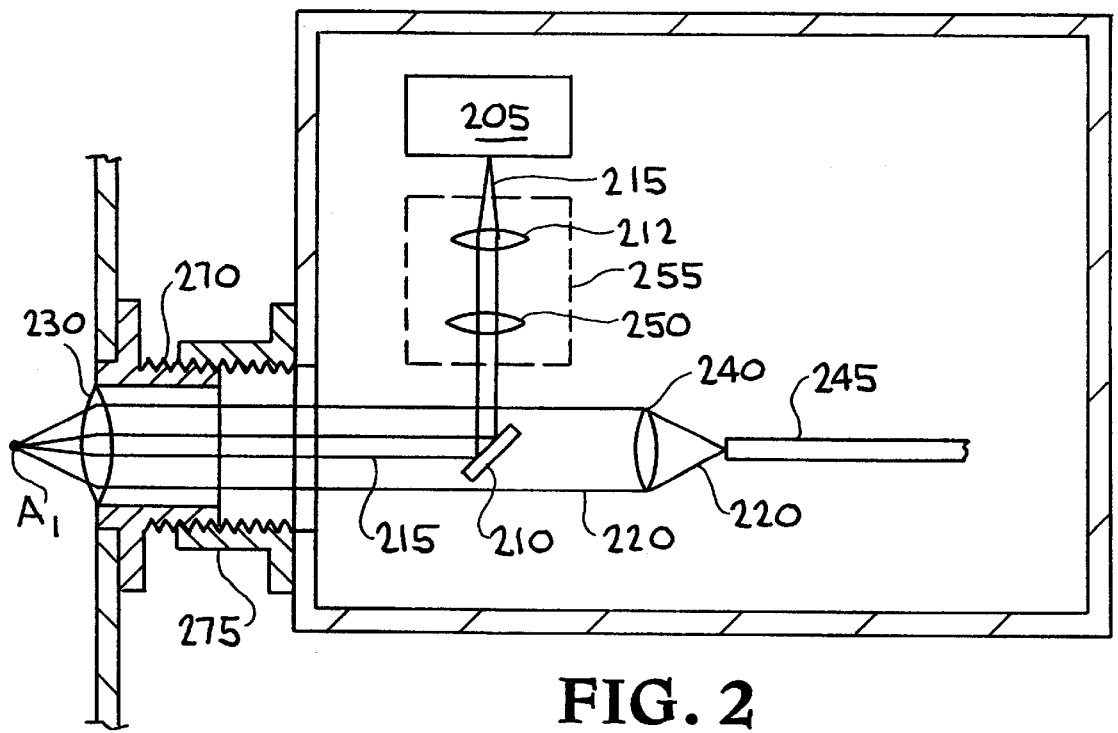
FIG. 2 shows a second embodiment of the instant invention.

A second embodiment of the instant invention is shown in FIG. 2. Here an input light beam 215 issues from light source 205 and is collimated by collimating lens 212. Collimated laser beam 215 is input to focusing lens 230 by means of inclined mirror 210. Input beam 215 can then be brought to a focus by focusing lens 230 onto point $A_i$ for analysis. The optical response of particles (not shown) at point $A_i$ can be collected by lens 230 in the form of a return beam 220 which is brought to a focus, by focusing lens 240, onto a light detector (not shown), such as a photodiode or charge coupled device, or onto a optical fiber cable or bundle 245 for transmitting light to a light detector. A beam expanding telescope 255 consisting of lenses 212 and 250 can be inserted into the input light beam 215 if desired. As set forth above, new analysis points $A_i$ (where i=2, ..., n) can be acquired by simply translating focusing lens 230 so that new analysis point $A_i$ is located at the focal point of the lens; no further changes or adjustments are required. This embodiment is particularly advantageous, because it permits the light source to be mounted at an angle relative to the beam axis, e.g., perpendicular, rather than in-line thereby permitting a more compact monitoring instrument.

Lens 130 or 230 can be translated by mechanical means such that new analysis locations can be acquired. These mechanical means can be, but are not limited to, a rack and pinion arrangement 160, which can be motor driven, or a screw arrangement wherein the lens retaining assembly 270 can be threaded and can be fitted into a receiving member 275, having spiral grooves, and acting in cooperation with lens retaining assembly 270 to translate lens 230 as lens 230 is rotated about its axis, or equivalents thereof.

Thus, the first and second embodiments of the present invention disclose means for coaxially separating counter-propagating light beams employing differential beam size or diameter and also maintain the alignment of the optical probe as it focuses on different analysis points within the flow stream.

From the foregoing description and examples, one skilled in the art can readily ascertain the essential characteristics of the present invention. In particular, it will be appreciated by those skilled in the art that the optical probe of the instant invention can be also be used with any of a variety of other optical techniques that rely on measuring the optical response at a point (or in a small volume or on a surface or interface) to an input optical signal. Optical techniques for which the present optical probe provides an advantage comprise; laser spark spectroscopy, Raman scattering, laser-induced fluorescence, Rayleigh scattering, Mie scattering and laser-induced incandescence. The description and examples are intended to be illustrative of the present invention and are not to be construed as limitations or restrictions thereon, the invention being delineated in the following claims.

We claim:

1. An optical probe, comprising:
   a) means for generating an input light beam;
   b) means for collimating the input light beam;
   c) focusing means for focusing the collimated input light beam onto an analysis location and for generating a collimated return light beam from the analysis location, the collimated return light beam having a common optical path with the collimated input light beam;
   d) means for separating the collimated input light beam from the collimated return beam employing differential beam diameters;
   e) means for collecting and focusing the separated collimated return light beam;
   f) means for transmitting the collected and focused return light beam to an analysis means; and
   g) means for translating said focusing means to a plurality of analysis locations without having to realign the optical probe.

2. The optical probe of claim 1, wherein said means for separating includes a mirror positioned coaxially with said focusing means and at an angle to the collimated input light beam such that the collimated input light beam reflected from the mirror is incident on the focusing means.

3. The optical probe of claim 1, wherein said means for separating includes a mirror positioned coaxially with said focusing means and at an angle to the collimated input light beam and wherein the mirror has an aperture therethrough permitting the collimated input light beam to pass through the mirror and onto the focusing means.

4. The optical probe of claim 3, wherein the mirror collects and subsequently reflects the collimated return light beam onto a transmitting means for transmitting the collimated return light beam to a detection means for analysis.

5. The optical probe of claim 4, wherein the surface of the mirror is curved.

6. The optical probe of claim 1, further including wavelength selection means for selecting wavelengths of the collimated return beam for analysis.

7. The optical probe of claim 1, further including a beam expanding telescope.

8. A method for focusing a collimated input light beam onto a plurality of locations for analysis while maintaining optical alignment, comprising the steps of:
   a) directing the collimated input light beam onto a focusing means;
   b) focusing the collimated input light beam onto an analysis location and generating a coaxial and counter propagating collimated return light beam;
   c) separating the collimated input light beam from the collimated return light beam employing differential beam diameters;
   d) transmitting the separated collimated return light beam to an analysis means; and
   e) translating the focusing means such that the collimated input light beam is focused consecutively to a plurality of locations.

9. The method of claim 8, wherein said step of directing comprises providing a mirror inclined at an angle to the input collimated light beam, such that the input light beam reflected from the mirror is incident on the focusing means.

10. The method of method of claim 8, wherein said step of separating comprises providing a mirror positioned coaxially with the focusing means and at an angle to the input light beam and wherein the mirror has an aperture therethrough permitting the input collimated light beam to pass through the mirror and onto the focusing means.

* * * * *